United States Patent
Shimosawa et al.

[11] Patent Number: 5,482,464
[45] Date of Patent: Jan. 9, 1996

[54] DENTAL RESIN SHEET

[76] Inventors: Shigeru Shimosawa, 3-11-33, Sone Minami-machi 1-chome, Toyonaka, Osaka; Akira Fujii, 6-611-607, Koyo-cho Naka 6-chome, Higashi-Nada, Kobe, Hyogo, both of Japan

[21] Appl. No.: 289,019

[22] Filed: Aug. 11, 1994

[30] Foreign Application Priority Data

Aug. 12, 1993 [JP] Japan ................................. 5-222211

[51] Int. Cl.⁶ ................................................. A61C 13/08
[52] U.S. Cl. .................................. 433/202.1; 433/203.1; 433/215; 433/226
[58] Field of Search ................................ 433/226, 227, 433/217.1, 202.1, 203.1, 212.1, 218, 215, 219

[56] References Cited

U.S. PATENT DOCUMENTS

| | | | |
|---|---|---|---|
| 3,265,202 | 8/1966 | Cornell | 433/202.1 |
| 4,433,959 | 2/1984 | Faunce | 433/222.1 |
| 5,151,044 | 9/1992 | Rotsaert | 433/202.1 |
| 5,183,397 | 2/1993 | Weissman | 433/226 |
| 5,183,403 | 2/1993 | Masuhara et al. | 433/9 |
| 5,308,243 | 5/1994 | Emmons | 433/203.1 |
| 5,332,390 | 7/1994 | Rosellini | 433/222.1 |

FOREIGN PATENT DOCUMENTS

| | | | |
|---|---|---|---|
| 703460 | 4/1931 | France | 433/202.1 |
| 5068687 | 3/1993 | Japan | 433/203.1 |

*Primary Examiner*—Cary E. O'Connor
*Attorney, Agent, or Firm*—Thompson, Hine & Flory

[57] ABSTRACT

Disclosed here is a dental resin sheet that is attached onto the surface of a tooth or the veneering crown to form the surface of the tooth or the crown. The dental resin sheet is constructed of a plurality of resin layers laminated into a uniform thickness, and the resin layers correspond to the layered structure of the tooth, one for the cervical, another for the dentin and another for the incisal. By laminating the layers of different shading in inclination with respect to the surface of the sheet, a shade of a tooth is achieved. A single elongated continuous sheet may be cut to a plurality of pieces of sheet each of which matches the configuration of a tooth. A single sheet may be configured to be shaped to the surface configuration of a tooth.

5 Claims, 3 Drawing Sheets

DENTAL RESIN SHEET

BACKGROUND OF THE INVENTION

1. Field of the Invention

The present invention relates to a novel dental resin sheet which is veneered onto the surface of a tooth or onto the crown to form the surface layer of the tooth or the crown.

2. Description of the Related Art

Rigid plastic shells have been widely used to cover teeth in a dental prosthetic treatment. In an actual treatment, a shell of which surface is beforehand shaped to match the surface a tooth is used; bonding agent is applied onto the surface of the tooth; and the shell is then attached onto the tooth after dental cement is plastered onto the tooth. Although the hard shell has beforehand been shaped to the tooth, the shell is usually unable to perfectly match the configuration of the tooth when it is attached, and thus, the shell would leave some gap between the inner surface of the shell and the outer configuration of the tooth. The cement is thus required to fill the gap.

During a dental treatment session, a patient is continually subjected to stress such as pains or mouth openings for treatment. Thus, the shorter the session, the better. Cement is available to fill the gap between the inner configuration of the shell and the tooth. The shell outer configuration, however, does not always match the original shape of the tooth that has had an intimate functional cooperation with other tooth in the patient mouth for a long time. With the shell, it is subjected to grinding and polishing. Such a treatment is sometimes time-consuming, and puts the patient under physical and metal pressure. Furthermore, the grinding and polishing operation can change the original shading of the shell.

In the production of a resin veneering crown, it is important to use resin that closely simulates the shading of the natural teeth of the patient. Ten or more shade guides are currently available. From among them, a shade guide that is near to the shading of the patient teeth is picked out. Each guide is numbered, and the number of the selected guide is referenced to select paste resin. In a commonly practiced procedure, opaque is applied onto the surface of the metal crown, and then an instrument is used to plaster resin onto opaque covered crown. In the final step, the resin is subjected to light for a certain period time if it is a lightcuring resin, and is heated for a certain period of time if it is a heat-curing resin. This concludes the production of the resin veneering crown.

The color of natural teeth is not uniformly shaded, but varied from location to location; for example, cervical, dentin and incisal are different in shading. Furthermore, the thickness of each tooth layers affects the surface shading. Furthermore, the shading of the tooth varies from person to person, and also with age. Thus, rather than a single type resin with a single shade, two to four resins with different shadings are used and prepared on a case-by-case basis so that the resulting shade may be as natural as the shading of the patient teeth.

In practice, however, matching faithfully the selected shade guide is a difficult task. Simulating accurately the natural shading and even surface irregularity of the tooth requires quite a lot of experience. Thus, difference in level of skill in dental technicians who have prepared crowns affects greatly acceptability of each crown. Thus, no uniform quality is assured.

SUMMARY OF THE INVENTION

It is the object of the present invention to provide material which shortens the dental treatment time by eliminating a cement plastering step in a dental prosthesis session of a natural tooth and which alleviates a patient's post-treatment feels. It is also another object of the invention to provide material which assures that no substantial difference is made in the acceptability of finished the resin veneering crown by the difference in the level of skill in dental technicians.

To achieve the above objects, the present invention basically comprises the step of laminating dental resin layers one on top of another to make a layered sheet with uniform thickness.

These and other objects, advantages and features of the present invention will become readily apparent to those skilled in the art from a study of the following description of preferred embodiments when read with the attached drawings and appended claims.

DESCRIPTION OF THE PREFERRED EMBODIMENTS

Figure 1:
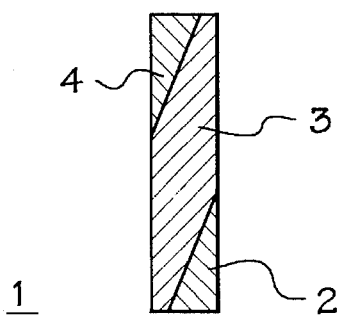
FIG. 1 is a cross-sectional view showing a preferred embodiment of a dental resin sheet according to the present invention.

Referring now to the drawings, preferred embodiments of the present invention are discussed below.

FIG. 1 is a thickness cross-sectional view showing a dental resin sheet 1 according to the present invention, wherein lightcuring resin layers 2 through 4 are laminated. The resin layers 2 through 4 are laminated in a manner that their mating faces are linearly inclined with respect to the surface of the dental resin sheet 1 as in FIG. 1. Resin layers 2 through 4 are different in shading to simulate the shading of the natural tooth; for example, they correspond to cervical, dentin, incisal. Specifically, resin layer 2 simulates the cervical of the tooth, resin layer 3 simulates the dentin of the tooth, and resin layer 4 simulates the incisal of the tooth. Since any tooth may be of a plurality of shades depending on location, rather than of a single shade, a plurality of typical shades are desirably prepared according to shade guides.

Figure 2:
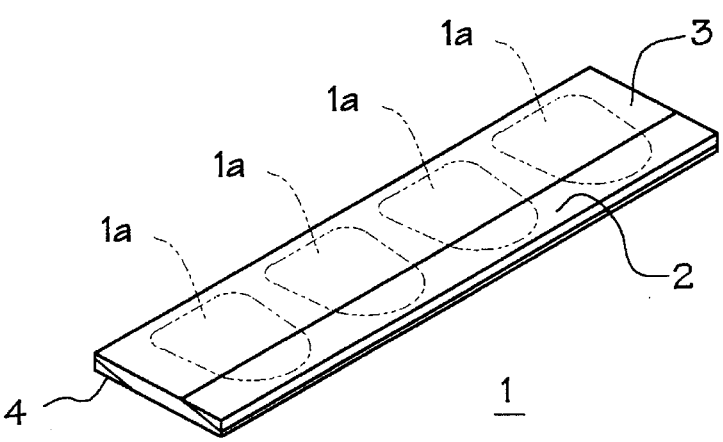
FIG. 2 is a perspective view showing the sheet of FIG. 1.

Referring to FIG. 2, the steps of applying the sheet are now discussed. A sheet 1 is cut to a plurality of resin sheets 1a that are shaped roughly to the tooth to be treated. It is important to cut through all resin layers of the laminated sheet 1 together. After applying opaque onto the surface of the tooth, the sheet 1a is attached onto the tooth using a spatula or by hand, so that the sheet 1a securely sticks onto the tooth until the original configuration is faithfully reproduced by the attached sheet 1. In this embodiment, the mother sheet 1 is an elongated one from which a plurality of sheets 1a are produced. The length of the sheet 1 may be arbitrarily set.

Figure 3:
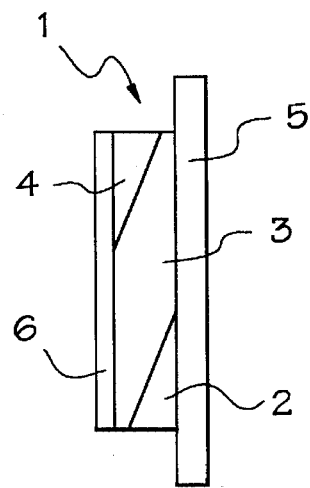
FIG. 3 is a side view showing an embodiment of the sheet suitably packed for storage.

Since the dental resin sheet 1 is made of lightcuring resin layers 2 through 4, it must be kept unexposed to light until its attachment to the tooth. If it is exposed, resin layers 2 through 4 may be photopolymerized. To keep the resin sheet 1 unexposed until its use, the sheet 1 is temporarily attached onto a mount 5 in a manner that its surface to be attached onto the tooth is interfaced to the mount 5 as in the embodiment shown in FIG. 3. The mount 5 is constructed of a light-screening material to cut off light. Light-transmitting film 6 is attached onto the surface of the sheet 1 opposite the mount 5. The sheet 1 thus mounted is stored in a light-screening container for storage. For use, the sheet 1 is peeled back from the mount 5, and then attached onto the tooth to which bonding agent has been applied beforehand. The light-transmitting film 6 may be removed immediately before photopolymerization. However, a more effective result may be achieved if the light-transmitting film 6 is removed after the resin sheet 1 gets photopolymerized. This is because the surfaces of the lightcuring resin layers 2 through 4 that would be otherwise exposed to air are protected from oxygen that could interfere with photopolymerization activity. If the light-transmitting film 6 is removed before completion of photopolymerization, oxygen interferes with photopolymerization activity on the surface of the sheet 1. Thus, incompletely photopolymerized surface results. To remove the incompletely photopolymerized layer, an additional step is required as in the conventional method. By removing the light-transmitting film 6 after the completion of photopolymerization, a polishing operation to remove the incompletely photopolymerized surface layer is dispensed with. This shortens the treatment time required. Furthermore, the light-transmitting film 6 protects the surface of the resin sheet 1, and thus assures that the surface of the sheet 1 is kept smooth when they make up the surface shape of the sheet 1.

Figure 4:
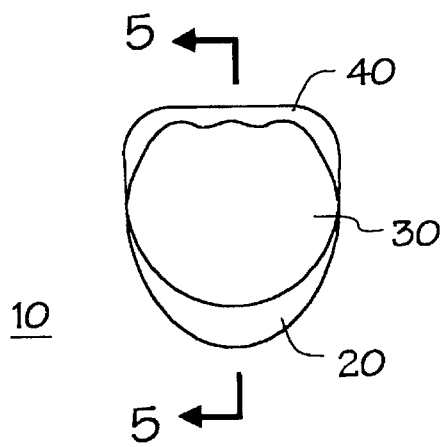
FIG. 4 is a front view showing another embodiment of the sheet according to the present invention.
Figure 5:
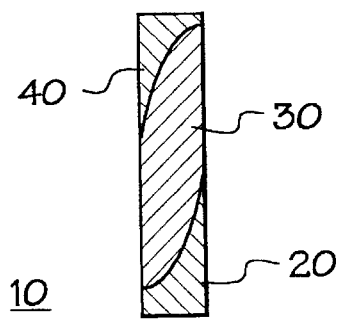
FIG. 5 is a cross-sectional view showing the sheet taken along in the direction of a line a—a in FIG. 4.

Another embodiment of the dental resin sheet is now discussed. FIG. 4 is a front view showing a resin sheet 10. In the same manner as the resin sheet 1 in the preceding embodiment, the resin sheet 10 is made of three laminated layers 20, 30 and 40. One sheet 10 corresponds to a tooth. As seen from the cross-sectional view in FIG. 5, however, the resin layers 20, 30 and 40 are laminated in a manner that their mating faces are curved. The resin sheet 10 thus constructed results in a more natural shading or gradation, and consequently can give a shading more looked like that of a tooth. The sheet 10, however, needs a high manufacturing technique, compared to the sheet 1. Which to use the sheet 1 or the sheet 10 may be at the option of each patient considering time and cost involved in the production.

The resin sheet 10 is constructed of lightcuring resin layers 20 through 40. In its storage condition, the resin sheet 10 is kept attached onto a mount in a manner that its surface to be attached to the tooth is interfaced to the mount, in a way similar to the embodiment shown in FIG. 3. Attached to the surface of the sheet 10 opposite its surface to the mount is a light-transmitting film.

Figure 6:
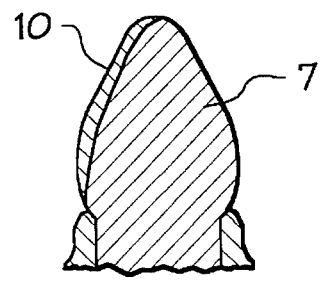
FIG. 6 is a cross-sectional view showing the relationship between a tooth bud and its sheet.
Figure 7:
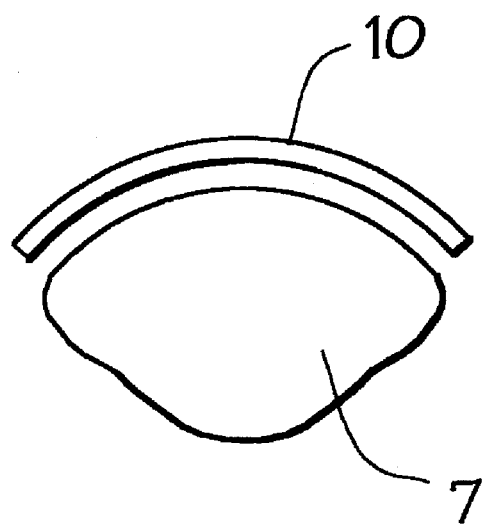
FIG. 7 is a plan view showing the relationship between the tooth bud and its sheet.

FIGS. 6 and 7 shows the step of attaching the sheet 10 onto the surface of a tooth 7 based on laminated veneer restoration method. Before bonding agent is applied onto a tooth 7 to be treated, the tooth 7 is cleaned, crusts such as sordes that collect on the tooth is removed, and, if necessary, the surface layer of the tooth is partly ground thin away. The sheet 10 is then attached onto the tooth 7. The sheet 10 is pressed by hand immediately after its attachment so that no air remains captured between the surface of the tooth and the sheet 10. The sheet 10 attached is subjected to light for a predetermined time of period until it is completely photopolymerized.

Figure 8:
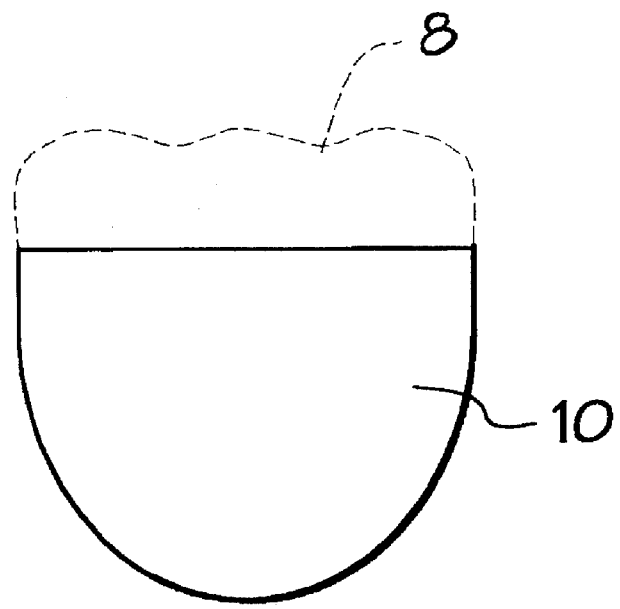
FIG. 8 is a front view showing the sheet that has been applied to a tooth of which tip portion is worn out.

Although the sheet 10 is cut as shown in FIG. 4, the portion 8 shown by dotted line in FIG. 8 is desirably cut away to make the sheet 10 when the tooth tip is already worn away.

In the above embodiment, the dental resin sheet 10 is applied to the front surface the tooth in the laminated veneer restoration method. It is contemplated that the sheet 10 is attached on the top of the tooth. It is also contemplated that the sheet 10 that is of the shade of another tooth is attached onto the tooth of which surface layer has been ground thin. The resin sheet also may be used as the surface for resin crown or resin veneer metal crown in the dental laboratory job.

In the above two embodiments, each sheet is made of three types of resin layers with three different shades. The number resin layers is not limited to three. Only two types of laminated resin layers sufficiently work. If the three laminated layers prove unsatisfactory, four laminated layers may be used. The sheet is not limited to lightcuring type; it may be other type of resin such as heatcuring resin. If one layer is constructed of a lightcuring type, the remaining layers should be of a lightcuring type; and if one layer is constructed of a heatcuring type, the remaining layers should be of a heatcuring type. The thickness of the sheet is preferably somewhere between 0.5 mm and 1.0 mm. The sheet that is in the region of 1.0 mm or 0.5 mm fails within the scope of the present invention.

What is claimed is:

1. A dental resin sheet for use in dental surface prothesis of a tooth or a veneering crown comprising:

a uniformly thick sheet made of a light curing resin having a plurality of dental laminated resin layers;

a mount; and a light transmitting film, wherein the dental resin sheet is attached to the mount on a first surface of the dental sheet until the dental sheet is mated with the tooth, and wherein the light transmitting film is attached to a second surface of the dental sheet.

2. The dental resin sheet according to claim 1 wherein the resin layers are of different shades and the resin layers are laminated in a manner such that the resin layers are inclined with respect to the cross-sectional thickness of the dental resin sheet.

3. The dental resin sheet according to claim 1 wherein the dental resin sheet is an elongated continuous sheet made of laminated resin layers and is cut into a plurality of pieces of dental resin sheet.

4. The dental resin sheet according to claim 1 wherein each piece of dental resin sheet is beforehand shaped to the a surface configuration of the tooth.

5. The dental resin sheet according to claim 1 wherein the dental resin sheet is kept in a light-screening container.

* * * * *